US008372890B2

(12) United States Patent
Terada et al.

(10) Patent No.: US 8,372,890 B2
(45) Date of Patent: Feb. 12, 2013

(54) FUNCTIONAL FOOD CONTAINING SODIUM TRICAFFEOYLALDARATE

(75) Inventors: Sumio Terada, Nerima-ku (JP); Kikuo Itoh, Nerima-ku (JP); Naoto Noguchi, Nerima-ku (JP); Takashi Ishida, Nerima-ku (JP)

(73) Assignee: Zenyaku Kogyo Kabushikikaisha, Tokyo (JP)

( * ) Notice: Subject to any disclaimer, the term of this patent is extended or adjusted under 35 U.S.C. 154(b) by 824 days.

(21) Appl. No.: 12/304,803

(22) PCT Filed: Jun. 18, 2007

(86) PCT No.: PCT/JP2007/062222
§ 371 (c)(1),
(2), (4) Date: Dec. 15, 2008

(87) PCT Pub. No.: WO2007/145356
PCT Pub. Date: Dec. 21, 2007

(65) Prior Publication Data
US 2009/0209649 A1     Aug. 20, 2009

(30) Foreign Application Priority Data

Jun. 16, 2006    (JP) ................................ 2006-168176

(51) Int. Cl.
A61K 31/045        (2006.01)
A61K 36/00         (2006.01)
(52) U.S. Cl. ........................................ 514/728; 424/725
(58) Field of Classification Search .................. 514/728; 424/725
See application file for complete search history.

(56) References Cited

FOREIGN PATENT DOCUMENTS

| JP | 8 175964 | 7/1996 |
|----|----------|--------|
| JP | 3039864 | 3/2000 |
| JP | 3039864 B1 * | 5/2000 |
| JP | 2001-19664 | 1/2001 |
| JP | 2001 19664 | 1/2001 |
| JP | 2002 68953 | 3/2002 |
| JP | 2003 231894 | 8/2003 |
| JP | 2006 151838 | 6/2006 |
| JP | 2006 273755 | 10/2006 |
| JP | 2006 273756 | 10/2006 |

OTHER PUBLICATIONS

The English Translation for JP 3039864 B1 (Kameyama et al.) May 2000.*
Terada, S. et al, "α-Glucosidase Inhibitory Active Components and Glucose Level Lowering Effect of Yacon Aerial Part Extract", Natural Medicines, vol. 57, No. 3. pp. 89-94 (2003) (with English abstract).
Aybar, M. J. et al., "Hypoglycemic Effect of the Water Extract of Smallantus sonchifolius (Yacon) Leaves in Normal and Diabetic Rats", Journal of Ethnopharmacology, vol. 74, No. 2, pp. 125-132 (2001).
Terada, S. et al, "The Constituents Relate to Anti-Oxidative and α-Glucosidase Inhibitory Activities in Yacon Aerial Part Extract", Kugaku Zasshi, vol. 126, No. 8, pp. 665-669 (2006) (with English abstract).
Yoshito Tanaka, et al., "Prevention of glucose toxicity in HIT-T15 cells and Zucker diabetic fatty rats by antioxidants", Proc. Natl. Acad. Sci. USA, vol. 96, Medical Sciences, Sep. 1999, pp. 10857-10862.
Mika Katoh, et al., "Alloxan Radical-Induced Generation of Reactive Oxygen Species in the Reaction System of Alloxan with Ascorbate", Yakugaku Zasshi, vol. 122, The Pharmaceutical Society of Japan, 2002, pp. 831-839, with partial English translation.
F. A. Moharram, et al., "Polyphenols of *Melaleuca quinquenervia* Leaves —Pharmacological Studies of Grandinin", Phytotherapy Research 17, 2003, pp. 767-773.
Yoshihiro Chuda, et al., "Structural Indentification of Two Antioxidant Quinic Acid Derivatives from Garland (*Chrysanthemum coronarium* L.)", J. Agric. Food Chem., vol. 44, No. 8, 1996, pp. 2037-2039.
Motoyo Ohnishi, et al., "Inhibition in Vitro Linoleic Acid Peroxidation and Haemolysis by Caffeoyltryptophan", Phytochemistry, vol. 47, No. 7, 1998, pp. 1215-1218.
Hiroshi Ohkawa, et al., "Assay for Lipid Peroxides in Animal Tissues by Thiobarbituric Acid Reaction", Analytical Biochemistry 95, 1979, pp. 351-358.
M. S. Blois, et al,. "Antioxidant Determinations by the Use of a Stable Free Radical", Biochim. Biophys. Acta, 18, 1955, pp. 1199-1200.
Mee-Hyang Kweon, et al., "Identification and Antioxidant Activity of Novel Chlorogenic Acid Derivatives from Bamboo (*Phyllostachys edulis*)", J. Agric. Food Chem., vol. 49, No. 10, 2001, pp. 4646-4655.
Soraya Solon, et al., "Free radical scavenging activity of *Lafoensia pacari*", Journal of Ethnopharmacology 72, 2000, pp. 173-178.
Marja P. Kähkönen, et al., "Antioxidant Activity of Plant Extracts Containing Phenolic Compounds", J. Agric. Food Chem. vol. 47, No. 10, 1999, pp. 3954-3962.
Makiko Takenaka, et al., "Caffeic Acid Derivatives in the Roots of Yacon (*Smallanthus sonchifolius*)", Journal of Agricultural and Food Chemistry, vol. 51, No. 3, 2003, pp. 793-796.
Takuo Okuda, et al., "Tannins in *Artemisia montana*, A. princeps and Related Species of Plant", Yakugaku Zasshi, vol. 106,1986, pp. 894-899, with partial English translation.

(Continued)

*Primary Examiner* — Kevin E Weddington
(74) *Attorney, Agent, or Firm* — Oblon, Spivak, McClelland, Maier & Neustadt, L.L.P.

(57) ABSTRACT

Components that demonstrate an α-glucosidase inhibitory activity and hyperglycemic inhibitory activity have clearly been provided from among the components included in Yacon. The present inventors found that as a result of screening for a strong anti-oxidant component in a Yacon aerial portion extract, an antioxidant activity was converged in a DIAION HP-20 column chromatography 50% methanol-eluted fraction of hot water extract. Thus, since a previously unidentified high-content component was confirmed, the present inventors conducted purification thereof, and thereby separated TCAA. As a result, this TCAA was found to be the component that demonstrates the α-glucosidase inhibitory activity and hyperglycemic inhibitory activity.

6 Claims, 4 Drawing Sheets

OTHER PUBLICATIONS

Michael N. Clifford, et al., "Characterisation of Caffeoylferuloylquinic Acids by Simultaneous Isomerisation and Transesterification with Tetramethylammonium Hydroxide", Food Chemistry 34, 1989, pp. 81-88.

E. Adeghate, et al., "Nitric oxide and neuronal and pancreatic beta cell death", Toxicology 153, 2000, pp. 143-156.

Tair Lapidot, et al., "Antioxidant and Prooxidant Effects of Phenolics on Pancreatic β-Cells in Vitro", J. Agric. Food Chem. vol. 50, No. 25, 2002, pp. 7220-7225.

Naohito Ogose, et al., "The Inhibitory Effect of the Food which Consists of the Extract from the Leaf and Stem of Yacon on the Postprandial Increase in Blood Glucose for Subjects with Normal Blood Glucose or Borderline Diabetes", Japanese Pharmacology & Therapeutics, vol. 34, No. 6, Jun. 20, 2006, pp. 737-746, with English Abstract.

Makiko Takenaka, et al., "Changes in the Concentration of Phenolic Compounds During Growing, Storing, and Processing of Yacon", Nippon Shokuhin Kagaku Kaishi, vol. 53, No. 12, 2006, pp. 603-611, with partial English translation.

Kazuhiko Uchiyama, et al., "Astaxanthin protects β-cells against glucose toxicity in diabetic db/db mice", Redox Report, vol. 7, No. 5, 2002, pp. 290-293.

* cited by examiner

Structure of TCAA $R_1=R_2=R_4$=caffeoyl, $R_3$=H
or
$R_1=R_3=R_4$=caffeoyl, $R_2$=H Data are expressed by the Mean ± S.E. of 4-5 rats.
*: $p<0.05$, **: $p<0.01$, compared with Maltose by Dunnett's test.

FUNCTIONAL FOOD CONTAINING SODIUM TRICAFFEOYLALDARATE

CROSS-REFERENCE TO RELATED APPLICATIONS

This application is a 371 of PCT/JP07/62222 filed Jun. 18, 2007 and claims the benefit of JP 2006-168176 filed Jun. 16, 2006.

TECHNICAL FIELD

The present invention relates to an α-glucosidase inhibitor, a hyperglycemic inhibitor, and a functional food containing tricaffeoylaldaric acid, as well as a production method for tricaffeoylaldaric acid.

BACKGROUND ART

Diabetes is a lifestyle-related disease that has been strongly associated with dietary habits. Specifically, even in Japan, mild cases of type II diabetes mellitus, which account for at least 90% of all diabetic individuals, continue to increase as dietary habits tend more towards meat-based diets. Moreover, as co-existing illnesses with diabetes, serious disorders of various organ systems, such as diabetic retinopathy, diabetic nephropathy, and diabetic neuropathy are known, and in addition thereto risk factors from circulatory disorders, such as arteriosclerosis, or myocardial infarctions may also have a significant impact on the life prognosis of the individual. Thus, whether or not blood glucose level can somehow be controlled on a daily basis is a major factor in determining the life prognosis or future quality of life (QOL) of these individuals.

Among daily diets, indigestible dextrin, wheat albumin, guava tea polyphenol, soy milk extract, L-arabinose, etc., are offered as food products having hyperglycemic inhibiting effects, and commercial food products including these have already been approved for labeling as special health foods. These functional foods have also attracted a lot of interest, since they demonstrate a high degree of safety, without the side effects, etc. as seen in medicaments. Thus, Yacon is offered as a functional material that is distinct from these.

Yacon (*Smallanthus sonchifolia*) is an Asteraceae plant that is indigenous to the Andes mountains. The present inventors have reported discovering a hyperglycemic inhibitory activity in hot water extract of an aerial part of Yacon, that α-glucosidase inhibitory activity is associated with the onset of such an effect, and that a dicaffeoylquinic acids (DCQAs) within the extract, such as 3,4-dicaffeoylquinic acid, have a strong or selective α-glucosidase inhibitory activity (refer to Non-Patent Document 1). Moreover, it has been reported that a tricaffeoylaltraric acid contained in Yacon shows activity as an anti-oxidative agent (refer to Patent Document 1).

Recently, it has been reported that the onset of diabetes is stimulated by the affects of active oxygen on the pancreatic islets of langerhans, and that these effects are inhibited by the administration of anti-oxidative substances (refer to Non-Patent Documents 2 and 3). Moreover, it has also been reported that blood glucose levels in a streptozotocin (STZ) induced diabetic mouse were decreased via a polyphenol with anti-oxidative activity (refer to Non-Patent Document 4). Caffeic acid and DCQAs are known to have an anti-oxidative activity (refer to Non-Patent Documents 5 and 6).

Patent Document 1: Japanese Patent No. 3039864;
Non-Patent Document 1: Terada S., Ito K., Taka M., Ogose N., Noguchi N., Koide Y, Natural Medicines, 57, 89-94 (2003);
Non-Patent Document 2: Tanaka Y, Gleason C. E., Tran P. O. T, Harmon J. S., Robertson R. P., Proc. Natl. Acad. Sci. U.S.A., 96, 10857-10862 (1999);
Non-Patent Document 3: Katoh M., Sakurai K., Fujimoto Y., YAKUGAKU ZASSHI, 122, 831-839 (2002);
Non-Patent Document 4: Moharram F. A., Marzouk M. S., El-Toumy S. A., Ahmed A. A., Aboutabi E. A., Phytother. Res. 17, 767-773 (2003);
Non-Patent Document 5: Chuda Y., Ono H., Ohnishi-Kameyama M., Nagata T., Tsushida T., J. Agric. Food Chem. 44, 2037-2039 (1996); and
Non-Patent Document 6: Ohnishi M., Morishita H., Toda S., Yase Y., Kido R., Phytochemistry, 47, 1215-1218 (1998).

DISCLOSURE OF THE INVENTION

Problems to be Solved by the Invention

However, among the components contained in Yacon, the conventional art described in the above-mentioned citations did not completely clarify which components demonstrated an α-glucosidase inhibitory effect, or which components exhibited a hyperglycemic inhibitory effect. Moreover, a method for effectively purifying components having the α-glucosidase inhibitory effect and the hyperglycemic inhibitory effect from Yacon at a specific yield ratio was also not established.

In view of the above-mentioned problems, the present invention aims to clearly provide components having the α-glucosidase inhibitory effect and the hyperglycemic inhibitory effect from the components contained in Yacon. Moreover, an object of the present invention is to provide a method for effectively purifying components having the α-glucosidase inhibitory effect and the hyperglycemic inhibitory effect from Yacon at a specific yield ratio.

Means for Solving the Problems

As a result of thorough experimentation in order to solve the above-mentioned problems, the present inventors were able to achieve the present invention by discovering that among the components contained in Yacon, tricaffeoylaldaric acid shows a superior α-glucosidase inhibitory effect and hyperglycemic inhibitory effect.

Specifically, according to the present invention, a tricaffeoylaldaric acid-containing α-glucosidase inhibitory agent is provided. This α-glucosidase inhibitory agent contains the tricaffeoylaldaric acid showing the superior α-glucosidase inhibitory effect, which allows for the activity of α-glucosidase to be preferably inhibited.

Moreover, according to the present invention, a food functional product containing the above-mentioned α-glucosidase inhibitory agent is provided. This functional food product contains the tricaffeoylaldaric acid demonstrating the superior α-glucosidase inhibitory effect, which allows for the activity of α-glucosidase to be preferably inhibited.

Furthermore, according to the present invention, a tricaffeoylaldaric acid-containing hyperglycemic inhibitory agent is provided. This hyperglycemic inhibitory agent contains the tricaffeoylaldaric acid showing the superior hyperglycemic inhibitory effect, which allows for an elevation in blood glucose levels to be preferably inhibited.

In addition, according to the present invention, the functional food product containing the above-mentioned hyperglycemic inhibitory agent is provided. This functional food product contains tricaffeoylaldaric acid showing the superior hyperglycemic inhibitory effect, which allows for an elevation in blood glucose level to be preferably inhibited Moreover, according to the present invention, a production method for tricaffeoylaldaric acid is provided which includes steps of:
a) extracting the tricaffeoylaldaric acid-containing extract from an aerial part of Yacon by employing a solvent containing a hydrophilic organic solvent or water;
b) solid-phase extracting a first tricaffeoylaldaric acid-containing fraction from the tricaffeoylaldaric acid-containing extract by employing an aromatic absorbent agent; and
c) solid-phase extracting a second tricaffeoylaldaric acid-containing fraction by employing gel filtration agent under conditions in which a pH of the tricaffeoylaldaric acid-containing fraction is set within a range of no less than pH 6 to no greater than pH 10.

According to this method, since the solid-phase extraction is conducted in combination with the aromatic absorbent agent and the gel filtration agent, using an aerial part of a Yacon in which the content of tricaffeoylaldaric acid is high, and since the pH is set within a range of no less than pH 6 to no greater than pH 10, by adding sodium hydroxide, sodium carbonate, sodium bicarbonate, etc. to the extract having a weakly acidic original pH of approximately pH 4.5 to pH 5 in order to stabilize the tricaffeoylaldaric acid at the time of gel filtration, a large quantity of a salt of the tricaffeoylaldaric acid may be purified at a specific yield ratio.

Furthermore, according to the present invention, a production method for the tricaffeoylaldaric acid-containing extract is provided which includes a step of extracting the extract containing tricaffeoylaldaric acid from an aerial part of Yacon under a temperature within a range of no less than 25° C. (room temperature) to no greater than 100° C., by employing a mixed solution of water and ethanol, in which the ethanol concentration is no less than 0% to no greater than 70% (v/v). According to this method, a tricaffeoylaldaric acid-containing extract with a high content of tricaffeoylaldaric acid can be purified in large quantities from the aerial part of a Yacon, in which the content of tricaffeoyladaric acid is high, via the employment of a mixed solution of alcohol and water.

In addition, according to the present invention, a production method for the tricaffeoylaldaric acid-containing extract is provided which includes a steps of:
a) extracting a tricaffeoylaldaric acid-containing basic extract with a pH within a range of no less than pH 8 to no greater than pH 10, using a basic solvent; and
b) generating an acidic tricaffeoylaldaric acid-containing extract by setting the pH of the basic extract at a pH of no less than pH 2 to no greater than pH 6.

According to this method, a tricaffeoylaldaric acid-containing extract with a high content of tricaffeoylaldaric acid can be effectively purified in large quantities at a specific yield ratio from the aerial part of a Yacon in which the content of tricaffeoylaltraric acid is high, via the extraction of tricaffeoylaldaric acid in a stabilized form, using a basic solvent.

Effects of the Invention

According to the α-glucosidase inhibitor of the present invention, or functional food product including this, because tricaffeoylaldaric acid is included therein, the activity of α-glucosidase may be preferably inhibited.

Moreover, according to the hyperglycemic inhibitor of the present invention, or the functional food product including this, because tricaffeoylaldaric acid is included, the elevation of blood glucose level may be preferably inhibited.

Furthermore, according to the production method for the tricaffeoylaldaric acid of the present invention, since the extraction is performed under specific conditions in combination with a specific solid-phase extraction, large quantities of tricaffeoylaldaric acid may be effectively purified at a specific yield ratio.

In addition, according to the production method of the tricaffeoylaltraric acid-containing extract of the present invention, since the extraction is performed with a specific solvent from the aerial portion of Yacon, in which the content of tricaffeoylaldaric acid is high, the tricaffeoylaldaric acid-containing extract with a high content of tricaffeoylaldaric acid can be effectively purified in large quantities at a specific yield ratio.

MODE FOR CARRYING OUT THE INVENTION

Figure 1:
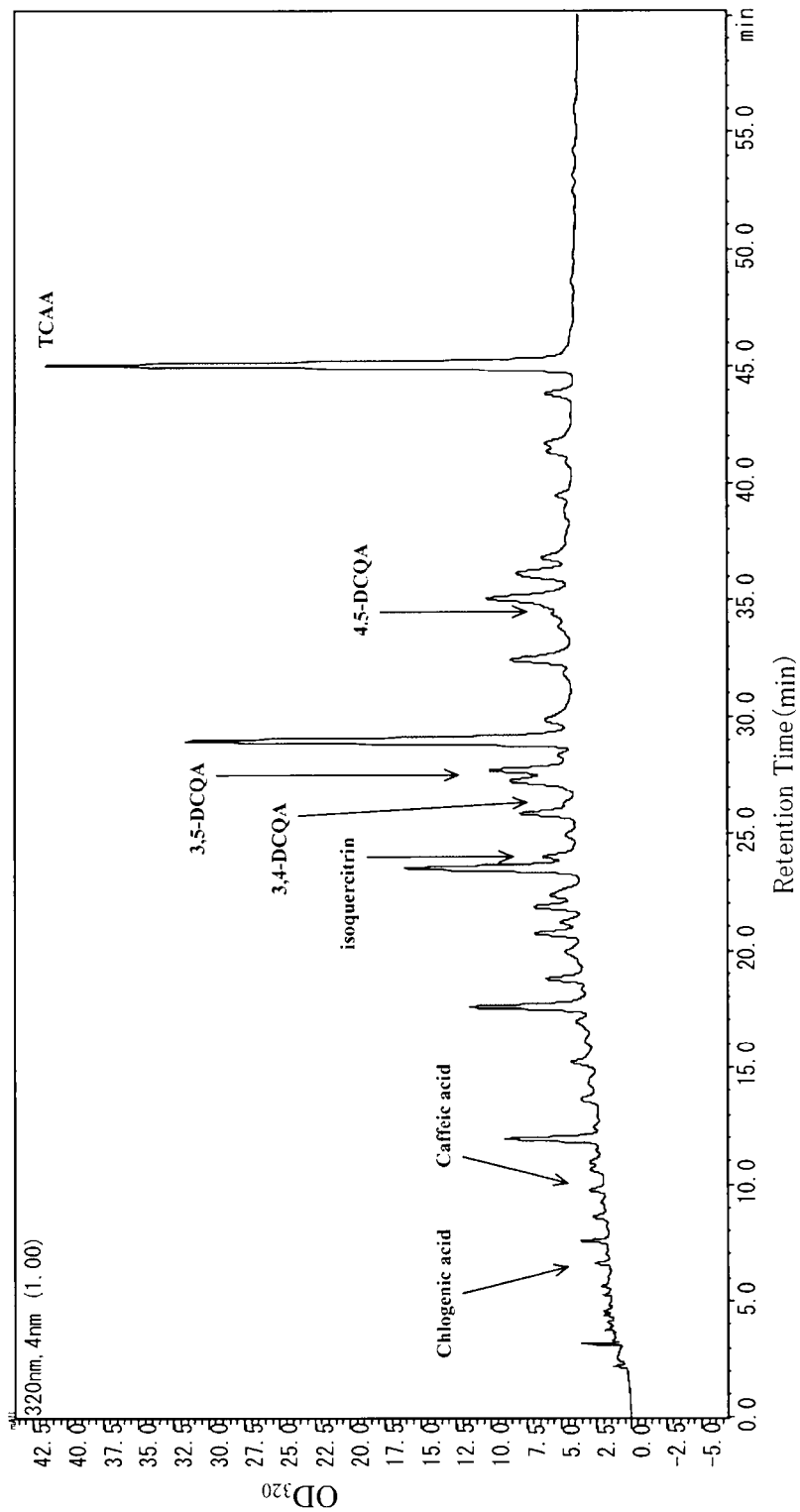
FIG. 1 shows an HPLC chromatogram of a DIAION HP-20 50% methanol-eluted fraction obtained from Yacon extract.

Hereinafter, the embodiments of the present invention will be explained.

In order to solve the above-mentioned problems, the present inventors have discovered a strong anti-oxidative effect comparable to that of α-tocopherol and (±)-catechin, when studying the aerial portion of Yacon extract. Thus, as a result of search for a component having such an activity, the present inventors discovered that an anti-oxidant activity was converged in a DIAION HP-20 column chromatography 50% methanol-eluted fraction of a hot water extract, in a similar to manner as that of the α-glucosidase inhibitory activity. Moreover, the present inventors discovered via HPLC analysis that the present fraction is a mixture of polyphenol components with a caffeoyl group, and detected components having an α-glucosidase inhibitory activity, such as DCQA. Accordingly, the present inventors simultaneously conducted purification of previously undetected components that were found in large quantites, and separation of 2,3,5-tricaffeoylaltraric acid, or 2,4,5-tricaffeoylaltraric acid (TCAA: tricaffeoylaltraric acid), which are known substances.

Moreover, since 2,3,5-tricaffeoylaltraric acid and 2,4,5-tricaffeoylaltraric acid are difficult to differentiate, they will hereinafter be defined as TCAA: tricaffeoylaltraric acid, in which they are both included. Accordingly, the description of "TCAA" within the present specification is one that includes 2,3,5-tricaffeoylaltraric acid, or 2,4,5-tricaffeoylaltraric acid.

The present inventors have evaluated anti-oxidant components of TCAA, in addition to other natural derivatives thereof, and discovered that when studying α-glucosidase inhibitory activity and hyperglycemic inhibitory activity, TCAA, a type of tricaffeoylaldaric acid, demonstrates a superior α-glucosidase inhibitory activity, and a superior hyperglycemic inhibitory activity.

Specifically, according to the present embodiment, a tricaffeoylaldaric acid-containing functional food product, and α-glucosidase inhibitory agent are provided. This functional food product and α-glucosidase inhibitory agent contains the tricaffeoylaldaric acid having the superior α-glucosidase inhibitory activity, which allows the activity of α-glucosidase to be preferably inhibited. Moreover, this functional food product may be labeled as being employed for inhibiting α-glucosidase, in order to raise consumer confidence and consumer convenience.

Furthermore, according to the present embodiment, a tricaffeoylaldaric acid-containing functional food product and hyperglycemic inhibitory agent is provided. This blood glucose elevation inhibitory agent contains the tricaffeoylaldaric acid having the superior hyperglycemic inhibitory activity, which allows for the elevation of blood glucose to be preferably inhibited. Moreover, this functional food product may be labeled as being employed for inhibiting hyperglycemia, in order to raise consumer confidence and consumer convenience.

Here, aldaric acids refer to acids obtained by formally oxidizing a carbon atom at each end of an aldose to a carboxylic acid. In addition, the aldaric acid may include allaric acid, altraric acid, glucaric acid, mannaric acid, guluronic acid, idaric acid, galactaric acid, taluronic acid (altraric acid), which are naturally occurring D-form isomers thereof.

Accordingly, the tricaffeoylaldaric acid is a compound in which an aldaric acid and a caffeic acid are ester linked, and is a generic name which includes TCAA, tricaffeoylallaric acid, tricaffeoylglucaric acid, tricaffeoylmannaric acid, tricaffeoylguluronic acid, tricaffeoylidaric acid, tricaffeoylgalactaric acid, or tricaffeoyltaluronic acid. Specifically, tricaffeoylaldaric acid is a generic name that includes isomers of TCAA, as well as several other varieties.

However, even among these, a TCAA in which a caffeic acid and altraric acid, which is an isomer of aldaric acid, are ester linked is particularly preferable as the tricaffeoylaltraric acid, as mentioned hereinafter. Accordingly, TCAA may not only include 2,3,5-tricaffeoylaltraric acid, but also 2,4,5-tricaffeoylaltraric acid.

TCAA, as mentioned hereinafter, has been confirmed as being contained within tricaffeoylaldaric acid purified from the aerial portion of Yacon via nuclear magnetic resonance spectra, or molecular formulae determined by precision mass spectrometry Moreover, a structural formula of TCAA is indicated below.

Structure of TCAA

[Formula 1]

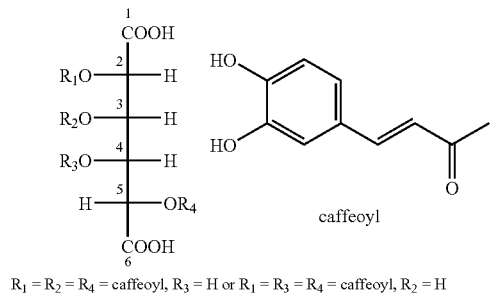

$R_1 = R_2 = R_4$ = caffeoyl, $R_3 = H$ or $R_1 = R_3 = R_4$ = caffeoyl, $R_2 = H$ Also, not to seem repetitive, but the above-mentioned isomer of tricaffeoylaldaric acid may include isomers such as tricaffeoylallaric acid, tricaffeoylglucaric acid, tricaffeoylmannaric acid, tricaffeoylguluronic acid, tricaffeoylidaric acid, tricaffeoylgalactaric acid, or tricaffeoyltaluronic acid, in addition to the above-mentioned TCAA. Accordingly, isomers of tricaffeoylaldaric acids other than TCAA may also be preferably employed in the α-glucosidase inhibitory agent, hyperglycemic inhibitory agent, and functional food product containing these, etc., of the present embodiment.

Moreover, it is preferable that the above-mentioned tricaffeoylaldaric acid is derived from Yacon, due to the high content of tricaffeoylaldaric acid contained therein. Moreover, it is preferable that the above-mentioned tricaffeoylaldaric acid is derived from the aerial portion of Yacon, due to the particularly high content of tricaffeoylaldaric acid contained in the aerial portion of leaves or stems, etc., even in Yacon.

Here, Yacon (*Smallanthus sonchifolia*) is an Asteraceae plant that is indigenous to the Andes mountains. Yacon is made up of two types of vegetative organs: stem tubers, which are typically utilized in reproduction (for the seedling); and subterranean root tubers, which are typically utilized in nutrient uptake. A corm (root tuber) portion contains a lot of water, has a crispy texture and subtle sweetness, and was used as a food source during the time of ancient Incans. On the other hand, the aerial portion of Yacon, such as that of the leaves or stems, etc., is utilized in salad or soup.

Moreover, not only is tricaffeoylaldaric acid included in the above-mentioned α-glucosidase inhibitory agent, hyperglycemic inhibitory agent, and functional food product containing these, but in addition thereto dicaffeoylquinic acids (DCQAs) may also be included. Since the dicaffeoylquinic acids (DCQAs) are contained in the hot water extract of the aerial portion of Yacon, similar to that of tricaffeoylaldaric acid, a strong and selective α-glucosidase inhibitory activity is demonstrated.

Furthermore, the above-mentioned α-glucosidase inhibitory agent, hyperglycemic inhibitory agent, and functional food product containing these, may additionally include other biologically active agents, food ingredients, or food additives, etc., as needed. Here, food additive refers to something that is employed by being added to, admixed to, or saturated into food products, or employed in an additional method thereof, for the preservation or processing of food products, or in the production process of food products, and which includes preservatives, sweeteners, and coloring agents, etc.

Moreover, the above-mentioned functional food product is included under health-promoting foods (specified health food products, or nutritional food products) as provided by the Ministry of Health, Labor, and Welfare. However, even if it were not included under health-promoting foods as provided by the Ministry of Health, Labor, and Welfare, so long as it was a food product demonstrating some superior physiological activity in comparison with conventional food products, it would be included under functional food products. Moreover, the labeling attached to the above-mentioned functional food product includes the required labeling for health-promoting foods as stipulated by the Ministry of Health, Labor, and Welfare, for example it is included on the label attached to the packaging/container of the functional food product.

The above-mentioned tricaffeoylaldaric acid is preferably derived from an extract of Yacon that is extracted by employing a solvent containing a hydrophilic organic solvent, or water. Specifically, it is preferable that it is extracted via an ethanol and water mixed solvent, or hot water extraction. Thus, the tricaffeoylaldaric acid-containing extract can be obtained from Yacon via extraction with the solvent containing the hydrophilic organic solvent, or water.

Furthermore, the abovementioned tricaffeoylaldaric acid may also be included as a sodium tricaffeoylaldarate, since extracting it as a sodium tricaffeoylaldarate is preferred so that the tricaffeoylaldaric acid is stabilized. At such a time, in order to further stabilize the tricaffeoylaldaric acid, it is preferable that the extraction as a sodium salt is performed under conditions in which the pH is set within a range of no less than pH 6 to no greater than pH 10.

For example, a production method for tricaffeoylaldaric acid may be provided which includes steps of:
a) extracting the tricaffeoylaldaric acid-containing extract from the aerial part of Yacon by employing a solvent containing a hydrophilic organic solvent or water;
b) solid-phase extracting a first tricaffeoylaldaric acid-containing fraction from the tricaffeoylaldaric acid-containing extract by employing an aromatic absorbent agent; and
c) solid-phase extracting a second tricaffeoylaldaric acid-containing fraction by employing a gel filtration agent under conditions in which the pH of the tricaffeoylaldaric acid-containing fraction is set within a range of no less than pH 6 to no greater than pH 10.

According to this method, since the solid-phase extraction is conducted in combination with the aromatic absorbent agent and the gel filtration agent using an aerial part of Yacon, in which the content of tricaffeoylaldaric acid is high, and since the pH is set within a range of no less than pH 6 to no greater than pH 10, in order to stabilize the tricaffeoylaldaric acid at the time of gel filtration, a large quantity of a sodium salt of the tricaffeoylaldaric acid may be effectively purified at specific yield ratio. At such a time, in order to further stabilize the sodium tricaffeoylaldarate, the second tricaffeoylaldaric acid-containing fraction is preferably eluted as a fraction containing a sodium tricaffeoylaldarate.

On the other hand, the conventional known HPLC employing method described in Patent Document 1 is one in which the purification of large quantities of tricaffeoylaldaric acid is difficult, and in particular, it is not a practical method for obtaining the above-mentioned tricaffeoylaldaric acid in gram units. Whereas, according to the method of the present embodiment, since the aerial part of Yacon having a high content of tricaffeoylaldaric acid is used, and since HPLC is not employed, the tricaffeoylaldaric acid can be purified in large quantities. Moreover, according to the method of the present embodiment, the purity of the tricaffeoylaldaric acid obtained may be improved by performing the solid-phase extraction in combination with the aromatic absorbent agent and the gel filtration agent. Furthermore, the tricaffeoylaldaric acid may be stabilized by setting the pH within a range of no less than pH 6 to no greater than pH 10 at the time of gel filtration, a superior yield ratio may be achieved that could not have achieved conventionally.

In addition, even in the method of the present embodiment, it is preferable that the extract is prepared by finely grinding the Yacon, and performing extraction via a mixed solvent of ethanol and water, or performing hot water extraction therefrom, in order to increase extraction efficiency. Although it is preferable that an aerial part of the Yacon in which there is a high content of tricaffeoylaldaric acid is employed, such as the stems or leaves thereof, the root tuber or stem of the Yacon may also be employed.

Although the extraction conditions are not particularly limited in any way, it is ordinarily preferable that the mixed solvent of ethanol and water employed is within a range of no less than 5 L to no more than 50 L, or that the hot water employed is within a range of no less than 5 L to no more than 50 L, per 1 kg of Yacon leaves or stems. Moreover, in cases where hot water is employed, it is preferable that the extraction is performed with the temperature of the hot water set within a range of no less than 40° C. to no more than 100° C. (boiling temperature), and for a time period within a range of no less than 0.1 hours to 24 hours. However, it may also be extracted from water that is only at room temperature, without employing hot water. Preferably, it is extracted at a temperature of no less than 60° C. to no greater than 80° C., and for a time period range of no less than 5 minutes to no greater than 40 minutes.

Whereas, in cases where a mixed solvent of ethanol and water is employed, it is preferable that extraction is performed with the mixed solvent composition of ethanol and water having an ethanol concentration set within a range of no less than 0% (v/v) to no greater than 90% (v/v), at a temperature within a range of no less than 25° C. (room temperature) to no more than 100C (boiling temperature), and for a time interval within a range of no less than 0.1 hours to 24 hours. The ethanol concentration may further be set within a range of no less than 10%, or no greater than 70%. Here, for example, methanol, 2-propanol, 1-propanol, acetone, dioxane, etc., may be employed as additional hydrophilic organic solvents substituting for ethanol. Preferably, the extraction is performed with the ethanol concentration within a range of no less than 30% (v/v) to no greater than 70% (v/v), at a temperature within a range of no less than 40° C. to no more than 90° C., and for a time interval within a range of no less than 0.1 hours to 1 hour. Alternatively, it is preferable that the extraction is performed with the ethanol concentration within a range of no less than 20% (v/v) to no greater than 50% (v/v), and at a temperature within a range of no less than 60° C. to no more than 80° C. Even more preferably, the extraction is performed with the ethanol concentration of 30% (v/v) at a temperature of 80° C. for 30 minutes.

Moreover, as a result of investigating various pH levels in order to further increase extraction efficiency, it was found that by performing extraction under basic conditions, the tricaffeoylaldaric acid was even more efficiently extracted. Specifically, by setting the pH of the extraction liquid at a pH of no less than 8 to no greater than 10 with the addition of a base to the solvent, then acidifying the solution by the addition of an acid, and next concentrating and lyophilizing the solvent, an extract with a high content of tricaffeoylaldaric acid may be obtained. Although, sodium carbonate, potassium carbonate, sodium hydroxide, potassium hydroxide, ammonia, etc. may be employed as the base, it is preferable that ammonia is added so that the pH of the extraction liquid is no less than pH 8 to no greater than pH 10. Moreover, the extraction temperature is room temperature and the extraction time is a short period of time in order to inhibit degradation of the tricaffeoylaldaric acid, with it preferably being extracted within 15 minutes. The acid employed in cases where returning the acidity may be hydrochloric acid, sulfuric acid, nitric acid, etc., with it preferably being hydrochloric acid. However, it is not particularly limited in any manner. The acidity may be set at a pH of no less than pH 2 to no greater than pH 6 by adding an acid, and preferably set at a pH of no less than pH 3 to no greater than pH 4.

Although the embodiments of the present invention are mentioned above, these embodiments are for illustrating examples of the present invention, in which various constructions other than those mentioned above may also be adopted.

For example, in the above-mentioned embodiment the production method by which the solid-phase extraction is performed in combination with an aromatic absorbent agent and gel filtration is not particularly limited in any manner, and thus the tricaffeoylaldaric acid may be purified by additionally performing column chromatography. Moreover, this solid-phase extraction is not particularly limited to a column method, and thus, any form such as a batch method, membrane method, etc., may also be performed. For example, when explaining an example of the column method, a test sample is passed through a solid-phase loaded column to trap a target component, then washed by an appropriate cleaning solution, so that the trapped target ingredient may be eluted by subsequently passing a eluting solution composed of alcohol, etc. Furthermore, prior to the solid-phase extraction, conditioning is performed by first passing a through the column a hydrophilic solvent, such as ethanol, so that a solid-phase surface may be moistened.

EXAMPLE(S)

Hereinafter, although the present invention will be further explained with reference to Examples, the present invention is not specifically limited to these Examples.

Example 1

Anti-oxidative Activity and α-Glucosidase Inhibitory Activity of TCAA

1. Experimental Method
1) Cultivation of Yacon
The Yacon was cultivated using a variety of Peruvian-A type Yacon corms donated by professor Teruo Tsukihashi, Ibaraki University, Department of Agriculture, at Central Research Field Laboratory, Zenyaku Kogyo, Co., Ltd., 2-choume Ohizumi-machi, Nerima-ku, Tokyo, 178-0062, Japan.
2) Type of Column
The substrates employed for column chromatography included DIAION HP-20 (Mitsubishi Chemical Corporation), LiChroprep RP-18 (Merck, Ltd.), TOYOPEARL HW-40F (Tosoh Corporation), and Sephadex LH-20 (Amersham Biosciences).
3) Separation of TCAA
From the aerial part of Yacon, 100 g was extracted by agitating IL of 70° C. hot water for 15 minutes, and cotton-filtered while hot. The filtered solution was concentrated and lyophilized, so that 17.3 g of dark brown colored powder was obtained. The total amount of this powder was loaded into a DIAION HP-20 column chromatograph (30 mmφ×200 mm), and then successively eluted with IL of water, IL of 50% methanol/water, and then IL of methanol, so that a 13.9 g of the concentrated lyophilized water-eluted fraction, a 2.21 g of the 50% methanol/ water-eluted fraction, and a 0.48 g of the methanol-eluted fraction were each obtained therefrom. Next, the TCAA amount in each of these was detected via HPLC analysis. An HPLC chromatogram of the DIAION HP-20 50% methanol-eluted fraction obtained from Yacon extract is shown in FIG. 1.

Subsequently, the 2.19 g of the 50% methanol/water-eluted fraction was twice divided and loaded into a LiChroprep RP-18 column chromatograph (35 mmφ×370 mm), and then successively eluted with methanol-5% acetic acid (3:7), then methanol-5% acetic acid (4:6). The collected methanol-5% acetic acid (4:6) eluted fraction was separated by TOYOPEARL HW-40F column chromatography (methanol-water=3:7 to 9:1), or Sephadex LH-20 column chromatography (methanol-water=8:2), to obtain 11.6 mg of TCAA as a pale yellow powder.
4) TCAA Identification Method
NMR was measured with JNM-EX400 (Japan Electron Optics Laboratories, Incorporated), using TMS as an internal standard. Moreover, doublet was abbreviated (d), and a double doublet was abbreviated (dd), respectively. High resolution FAB-MS was measured by JMS-SX102A (Japan Electron Optics Laboratories, Incorporated). UV spectra was measured by UV-2550 (Shimadzu Corporation), and specific rotation was measured by SEPA-300 (Horiba, Ltd.), respectively. HPLC analysis was conducted with an LC-10Atvp pump (Shimadzu Corporation), an SPD-M10Avp UV/Photo-diode Array Detector (Shimadzu Corporation), a CTO-10Asvp column oven (Shimadzu Corporation), or an SCL-10Avp System Controller (Shimadzu Corporation).

5) Determining the Amount of TCAA within the Extract of the Aerial Portion of Yacon.

The amount was determined under HPLC conditions, in which, column: YMC ODS-A 120-S5 (4.6 mmφ×150 mm); mobile phase: mixed solution of tetrahydrofuran (THF)—0.1% phosphoric acid (7:3); column temperature: 40° C.; flow rate: 1.0 ml/min; and detection wavelength: 332 nm.

Specifically, approximately 0.1 g of the extract was precisely measured, and dissolved in the mobile phase to prepare exactly 50 ml of test solution. Alternatively, approximately 0.01 g of a TCAA reference standard separated and purified by the above-mentioned method was precisely measured, dissolved in THF to prepare exactly 50 ml. After 15 ml of 0.1% phosphoric acid was added to 2 ml of this solution and mixed, the mobile phase was added to prepare exactly 50 ml as the standard solution. The test solution and standard solution were filtered with a 0.45 μm pore size membrane filter, 20 μl of each of these was injected into an HPLC, the peak areas AT and AS of TCAA in each solution were measured, and the amount of TCAA in 1 g of the extract was calculated via the below-mentioned formula.

$$\text{Amount of } TCAA \text{ (mg) in 1 g of Extract} =$$
$$\text{Amount of reference standard recovered (mg)} \times f \times$$
$$(1/25) \times (AT/AS) \times (1 \text{ g/grams of extract recovered});$$

Moreover, f: Purity of reference standard (%)/100
6) Brain Homogenate Auto-oxidation Test
Determined via a thiobarbituric acid method that was based on the method of Ohkawa, et al. (Reference Document 2)
7) 1,1-Diphenyl-2-picrylhydrazyl (DPPH) Radical Scavenging Test
Determined based on the method of Blois, et al. (Reference Document 3)
8) Glycosidase Inhibitory Activity Test
Determined via a method whereby α-amylase, maltase, and sucrase inhibitory activities were all disclosed in the abovementioned report (Non-Patent Document 1).

2. Experimental Results
When the anti-oxidative activity of the water-eluted fraction, 50% methanol/water-eluted fraction, and methanol-eluted fraction obtained by subjecting the extract of the aerial portion of Yacon to DIAION HP-20 column chromatography were each respectively examined, as indicated in Table 1, it was discovered that the activity was converged in the 50% methanol-eluted portion.

TABLE 1

Antioxidant activities of fractions and phenols from Yacon extract

| sample | Inhibitory Activities on Lipid Peroxidation IC$_{50}$: μg/ml | DPPH Radical Scavenging Activities EC$_{50}$: μg/ml |
|---|---|---|
| Yacon hot water extract | 6.65 | 15.38 |
| HP20-water | 20.96 | 32.19 |
| HP20-50% MeOH | 1.9 | 2.78 |
| HP20-MeOH | 24.24 | 13.12 |
| 3,4-DCQA | 1.48 (2.87) | 0.91 (1.76) |
| 3,5-DCQA | 2.18 (4.23) | 0.87 (1.69) |
| 4,5-DCQA | 3.38 (6.55) | 0.89 (1.72) |
| TCAA | 0.49 (0.70) | 0.69 (0.99) |
| isoquercitrin | 6.64 (14.31) | 1.53 (3.30) |
| chlorogenic acid | 13.21 (37.32) | 1.13 (3.19) |
| (±)-catechin | 13.69 (47.16) | 1.56 (5.37) |
| α-tocopherol | 71.24 (165.67) | 5.65 (13.14) |
| caffeic acid | 9.97 (55.34) | 4.39 (24.32) |
| enzogenol | 2.17 | 1.94 |
| ellagic acid | 0.56 (1.85) | 0.51 (1.69) |

( ): μM

When this fraction was multi-wavelength analyzed by an HPLC connected to a UV/Photodiode Array Detector a number of components with maximum absorbencies around 290 nm and 330 nm were present, and thus it was presumed that the 50% methanol-eluted fraction was comprised of caffeoyl groups. In addition to the α-glucosidase inhibitory active components reported in the above-mentioned report (Non-Patent Document 1), such as 3,4-DCQA; 3,5-DCQA; 4,5-DCQA; isoquercitrin; etc., being confirmed in this fraction, as shown in FIG. 1, since a previously unidentified high content containing component was detected, the separation and purification thereof were performed via column chromatography, and $^1$H and $^{13}$C-NMR data was obtained.

Figure 2:
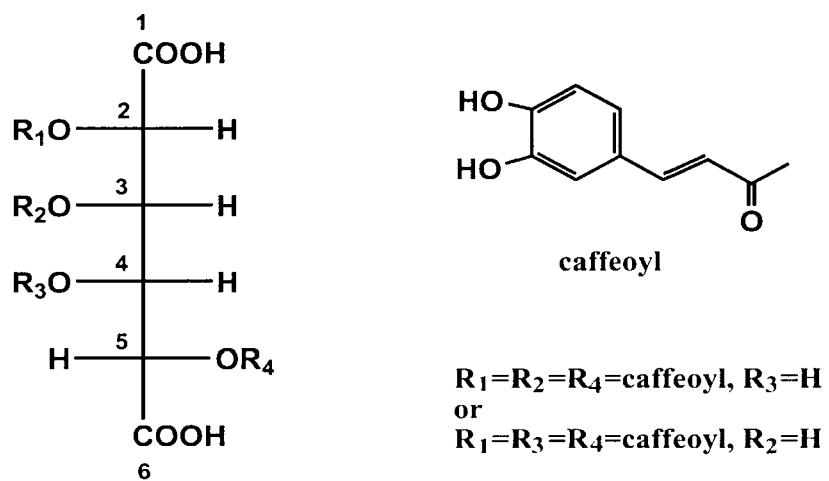
FIG. 2 shows a view explaining a structural formula of tricaffeoylaltraric acid (TCAA), which is a type of tricaffeoylaltraric acid.

The results obtained by a TCAA identification method are indicated below. From a comparison between this data and that of the literature (Reference Document 7), the unidentified component was identified as TCAA (FIG. 2), which was reported as a substance with anti-oxidative activity that was separated from a Yacon root tuber (Reference Document 8). Specifically, the unidentified high content containing component was confirmed as being 2, 3, 5-tricaffeoylaldaric acid; or 2, 4, 5-tricaffeoylaldaric acid.

Pale Yellow Powder $[\alpha]_D$+31° (c=0.2, methanol)

High Resolution FAB-MS (negative) m/z: 695.1200 (M$^+$−H) for $C_{33}H_{28}O_{17}$ UV λmax (EtOH) nm (log ε): 244 (4.28), 328 (4.50)

$^1$H-NMR (CD$_3$OD) δ: 4.84 (1H, dd, J=9.0, 2.0 Hz), 5.28 (1H, d, J=2.0 Hz), 5.65 (1H, dd, J=9.0, 2.0 Hz), 5.66 (1H, d, J=2.0 Hz), 6.22 (1H, d, J=15.9 Hz), 6.366 (1H, d, J=15.9 Hz), 6.371 (1H, d, J=15.9 Hz), 6.74(1H, d, J=8.3 Hz), 6.77 (1H, d, J=8.0 Hz), 6.78 (1H, d, J=8.3 Hz), 6.91 (1H, dd, J=8.3, 1.9 Hz), 6.970 (1H, dd, J=8.3, 1.8 Hz), 6.974 (1H, dd, J=8.3, 1.8 Hz), 7.02 (1H, d, J=1.9 Hz), 7.08 (1H, d, J=1.9 Hz), 7.09 (1H, d, J=1.9 Hz), 7.53 (1H, d, J=15.9 Hz), 7.64 (1H, d, J=15.8 Hz), 7.66 (1H, d, J=16.1 Hz)

$^{13}$C-NMR (CD$_3$OD) δ: 69.9, 72.7 (2C), 73.1, 113.9, 114.1, 114.2, 115.3 (3C), 116.5 (3C), 123.4 (2C), 123.5, 127.6, 127.7, 127.8, 146.8 (2C), 146.9, 148.2, 148.40, 148.43, 149.8, 149.9 (2C), 167.4, 168.1, 168.4, 170.4, 171.6

The anti-oxidative activity of the isolated TCAA and DCQAs were evaluated via a lipid peroxide production inhibitor test and DPPH radical scavenging test, as well as the natural products with anti-oxidative activity. As a result thereof, the lipid peroxide production inhibitory activity of TCAA was the strongest, with an activity thereof being 2.5 times greater than that of ellagic acid, and 68 times greater than that of (±)-catechin in comparative molar concentrations. Moreover, the DPPH radical scavenging activity of TCAA and DCQA is equivalent to that of chlorogenic acid (Reference Document 4), ellagic acid (Reference Document 5), and enzogenol (Reference Document 6), and stronger than that of α-tocopherol (Table 1).

Whereas, although the α-glucosidase inhibitory activity was weak with respect to sucrase and amylase inhibitory activity (IC$_{50}$>1000 μg/ml, IC$_{50}$=420 μg/ml, respectively), it showed stronger inhibitory activity with respect to maltase (IC$_{50}$=49 μg/ml), and ⅟19 the activity when compared to an acarbose control.

The resulting amount of TCAA determined from the extract of the aerial portion of Yacon was 0.25%, and a contribution ratio was calculated as being 30% with respect to the α-glucosidase inhibitory activity (IC$_{50}$=5.8 mg/ml) of the extract of the aerial portion of Yacon.

3. Discussion

Although TCAA with strong α-glucosidase inhibitory activity and anti-oxidative activity that was separated from the aerial portion of the present Yacon had already been reported and isolated from the root tuber of the same Yacon (Reference Document 7), it was the first time that α-glucosidase inhibitory activity had been confirmed.

Moreover, DCQAs are known to be included in coffee beans (Reference Document 10), or many Asteraceae plants, such as garland chrysanthemum (Non-Patent Document 4), Artemisia (Reference Document 9), and thus cannot be said to be Yacon specific components in which α-glucosidase inhibitory activity is present. However, since TCAA has not been previously reported as being separated from plant varieties other than Yacon, and since the content accounted for within the extract is also high, it is believed to be the principal component involved in the α-glucosidase inhibitory activity of Yacon extract.

Furthermore, TCAA demonstrates a stronger lipid peroxide production inhibitory effect than (±)-catechin, and demonstrates a radical scavenging effect equivalent to that of α-tocopherol.

Conventionally, it has been said that the recurrence of a postprandial hyperglycemic condition damages pancreatic β cells, leads to impaired insulin secretion along with a reduction in pancreatic β cell volume, causes further deterioration of glucose tolerance in Type II diabetes, and is a transition to diabetes mellitus, as indicated in fasting hyperglycemia (Non-Patent Document 2). Moreover, that pancreatic β cell exhaustion is inhibited by antioxidants has been frequently reported (Reference Document 11), and thus a similar effect had been anticipated, even in TCAA.

As mentioned above, the Yacon aerial portion contained a large quantity of a component having both a maltase selective α-glucosidase inhibitory activity and an antioxidant activity, and which is thought to be a useful material in the prevention of the onset of diabetes.

Example 2

Production Method for Extract Extracted from the Aerial Portion of Yacon

1) Example of an Extraction Via Water-ethanol

The aerial portion of Yacon (100 g) was added to 4 L of an water-ethanol (7:3) mixed solution heated to 80° C., and suction filtered after being agitated for 15 minutes at that temperature. The filtrate was concentrated under vacuo, and the concentrated solution was lyophilized, to obtain 29.51 g of extract. Since the amount of TCAA within 1 g of that extract was 2.8 mg, the total amount of TCAA extracted from the 100 g of the aerial portion of Yacon was 82.64 mg.

2) Example of Extraction Via a Basic Solvent:

The aerial portion of Yacon (100 g) was added to 2 L of 0.28% aqueous ammonia, and suction filtered after being agitated for 15 minutes at room temperature. The filtrate was concentrated under vacuo after the pH was set at 3.0 with 2N hydrochloric acid, and the concentrated solution was lyophilized, to obtain 40.35 g of extract. Since the amount of TCAA within 1 g of that extract was 3.79 mg, the total amount of TCAA extracted from the 100 g of the aerial portion of Yacon was 152.93 mg.

Example 3

Production Method for TCAA

A methanol-water (1:1) mixed solution was added in an amount of 1500 L per 150 kg of Yacon stems and leaves, and filtered after being allowed to stand overnight at room temperature. The filtrate was concentrated under vacuo, to obtain 35 L of a fluid extract. The fluid extract (5 L) was passed through a DIAION HP-20 (Mitsubishi Chemical Corporation) column (17ϕ×40 cm), eluted with 30 L of water, and then eluted with 25 L of the methanol-water (1:1) mixed solution. The methanol-water (1:1) eluted-fraction was collected, and concentrated under vacuo, to obtain 3 L of a 50% methanol-eluted fraction. The resulting dry weight was measured by lyophilizing a portion thereof, and the 50% methanol-eluted fraction found to be 211 g.

The 50% methanol-eluted fraction (3 L) was passed through a Polyamide C-200 (Wako Pure Chemical Industries, Ltd.) column (17ϕ×35 mm), first eluted with 25 L of water, next eluted with 25 L of methanol, then eluted with 10 L of methanol containing 0.1% aqueous ammonia, and finally eluted with 25 L of methanol containing 0.5% aqueous ammonia. The eluate was collected in 5 L aliquots, and detection of TCAA was conducted via HPLC (Method A). The fractions containing TCAA were recovered, concentrated in vacuo, and then lyophilized to obtain 28.4 g of a TCAA containing fraction.

The TCAA containing fraction was dissolved in 150 ml of water, the pH was set at 8.5 by adding 1 mol/L of $Na_2CO_3$ while measuring with a pH meter, then it was passed through a Sephadex LH-20 (Amersham Biosciences) column (5.0ϕ×70 cm), and eluted with a methanol-water (3:7) mixed solution. After being eluted with 500 ml, the eluate was collected in 15 ml aliquots, and detection of TCAA was conducted via HPLC (Method A). The fractions containing TCAA were recovered, concentrated in vacuo, and then lyophilized to obtain 5.71 g of a TCAA-sodium containing fraction. The purity via HPLC (Method B) was 92%.

This 5.71 g of TCAA-sodium containing fraction was dissolved in approximately 30 ml of a methanol-water (3:7) mixed solution, passed through a TOYOPEARL HW-40 (Tosoh Corporation) column (5.0ϕ×34 cm), and then eluted with a methanol-water (3:7) mixed solution. After being eluted with 200 ml, the eluate was collected in 15 ml aliquots, and detection of TCAA was conducted via HPLC (Method B). The fractions containing TCAA with a purity of at least 94% were recovered, concentrated in vacuo, and then lyophilized to obtain 4.14 g of a TCAA-sodium containing fraction. The purity via HPLC (Method B) was 95%.

The 4.14 g of TCAA-sodium containing fraction was dissolved in approximately 20 ml of a methanol-water (3:7) mixed solution, passed through a Sephadex LH-20 (Amersham Biosciences) column (5.0ϕ×70 cm), and then eluted with a methanol-water (3:7) mixed solution. After being eluted with 500 ml, the eluate was collected in 12 ml aliquots, and detection of TCAA was conducted via HPLC (Method B). The fractions containing TCAA with a purity of at least 97% were recovered, concentrated in vacuo, and then lyophilized to obtain 2.48 g of a TCAA-sodium containing fraction. The purity via HPLC (Method B) was 97%.

From this TCAA-sodium containing fraction, 300 mg was dissolved in 15 ml water, filtered with filter paper, then 10.5 ml of 0.1 mol/L hydrochloric acid was added drop-wise to the filtrate, and allowed to stand at room temperature for one hour. The precipitated crystals were filtered off, transferred to a brown bottle after being washed with 20 ml of water, and concentrated in vacuo at −40° C. to obtain 177 mg of TCAA. The purity via HPLC (Method B) was 98.8%.

HPLC (Method A)
Column: YMC-Pack R-ODS-5-A (4.6ϕ×250 mm)
Mobile Phase Acetonitrile-5% Acetic Acid (2:8) to (3:7), 20 minute linear gradient
Flow Rate: 1 ml/min
Detector: Ultraviolet Absorptiometer (Examined Wavelength: 332 nm)

HPLC (Method B)
Column: TSK-gel ODS-80™ (4.6ϕ×150 mm)
Mobile Phase: THF-0.1% Phosphoric Acid (3:7)
Column Temperature: 40° C.
Flow Rate: 1 ml/min
Detector: Ultraviolet Absorptiometer (Examined Wavelength: 332 nm)

Example 4

Hyperglycemic Inhibitory Action of Maltose-Loading TCAA in Rat

The present inventors confirmed that the abovementioned extract of Yacon leaves and stems demonstrates a hyperglycemic inhibitory effect, as shown in the above report (Non-Patent Reference 1), and further clarified that TCAA that is purified and isolated from the leaves and stems of Yacon demonstrates an α-glucosidase inhibitory effect, as shown in Examples 1 and 2. In Example 4, in order to show the effect of TCAA towards blood glucose, the maltose-loading hyperglycemic inhibitory action was investigated using a normal healthy rat.

1. Materials

1) Test Substance: With regard to TCAA, Yacon hot water extract was passed through an HP-20 column chromatograph, then eluted with water, and finally eluted with 50% methanol to obtain a polyphenol fraction. This fraction was separated by being passed through a Sephadex LH-20, and eluted with 40% methanol/water, so that the total amount of TCAA contained therein was recovered during confirmation of TCAA with HPLC. Then, the rough TCAA fraction was passed through a HW-40 column chromatograph, separated with 40% methanol/water during confirmation of TCAA with HPLC in a similar manner, and components other than TCAA were removed. This was further passed through a LiChroprep RP-18 column chromatograph, and purified with 5% acetic acid-methanol (3:7) to obtain TCAA (Purity: 91%, and Maltase Inhibitory Activity: $IC_{50}$=61 μg/ml). Moreover, the maltose employed was purchased from Wako Pure Chemical Industries, Ltd.

2) Animals: One group of five SD (IGS) 7 week old male rats was employed.

2. Experimental Method

1) Configuration of the Treatment Group (1) Control Group (Maltose Only)

(2) Maltose+TCAA (600 mg/kg×2)

(3) Maltose+TCAA (300 mg/kg×2)

(4) Maltose+TCAA (150 mg/kg×2)

2) Preparation of Test Substance

Maltose was weighed to an amount of 1.5 g, dissolved in 15 ml of distilled water, and administered by gavage at a dosage of 1 g/10 ml/kg. Then TCAA was administered in two doses, a first dosage in which it was administered in a maltose solution, and then a second dosage in which it was dissolved in distilled water, with both dosages being at ratios of 150 mg/10 ml, 300 mg/10 ml, and 600 mg/10 ml, respectively, and administration thereof by gavage at a dosage of 10 ml/kg.

Figure 3:
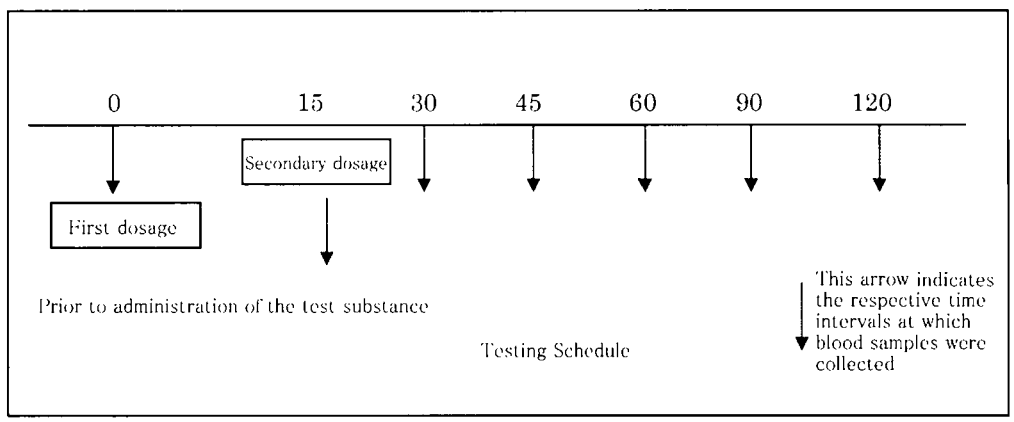
FIG. 3 is a schematic diagram showing an experimental schedule for evaluating a TCAA hyperglycemic inhibitory effect of maltose-loading in a rat.

3) Test System (FIG. 3)

After blood samples were collected from rats that fasted for 17 hours prior to administration of the test substance (0 time), the test substance was administered. Fifteen minutes later the second dosage was administered, with blood samples being taken soon thereafter (specifically, 15 minutes later), 30 minutes thereafter, 45 minutes thereafter, 60 minutes thereafter, 90 minutes thereafter, and 120 minutes thereafter, respectively, and then blood glucose levels being measured with a Glucocard (Aventis Pharma, Limited).

3. Test Items

When measuring blood glucose levels at the times that each of the samples were collected, the change in blood glucose (A) was calculated by subtracting the blood glucose level prior to the administration (0 time) from the blood glucose levels after the administration of the test substance, and determining the maximum serum concentration ($\Delta C_{MAX}$) and area under the blood glucose curve ($\Delta AUC$).

4. Statistical Analysis

The blood glucose values obtained by the present experiment were averaged, the standard error of the mean was calculated, and a two-group comparison was made with the control group. The statistical test method was via the Bartlett method, with the variance of the measured values being statistically verified within a 95% confidence limit, and the Student's t-test only being conducted in cases of equal variance, to determine that p<0.05 was a statistically significant change.

5. Changes in Blood Glucose

Figure 4:
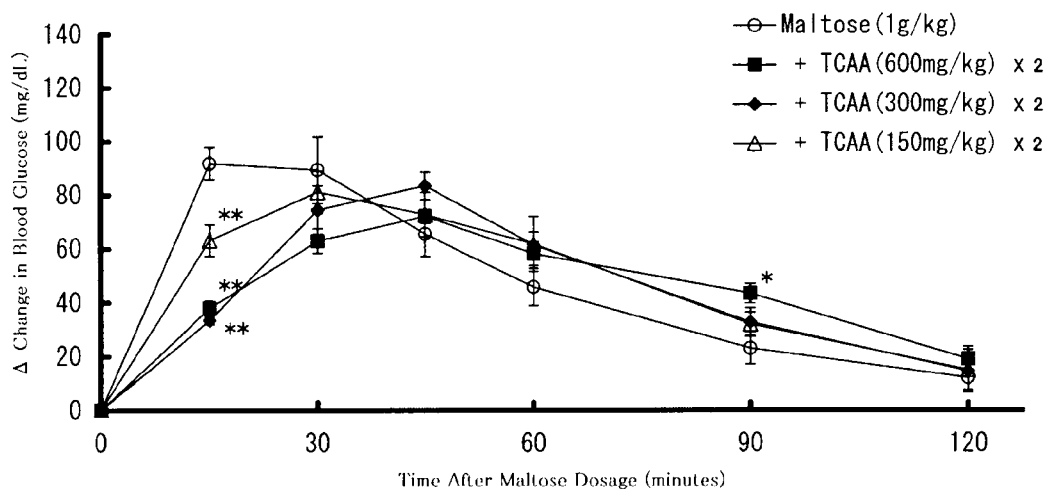
FIG. 4 is a graph showing changes in blood glucose levels after maltose-loading in a rat.

The changes in blood glucose are indicated in FIG. 4. A drastic increase in blood glucose via maltose-loading in the control group was seen at 15 minutes, and that increase was significantly inhibited in each respective TCAA dosage group (p<0.01). Whereas, an obvious increase in the 90 minute values of the 600 mg/kg TCAA group was seen when compared to that of control group.

6. AUC and $C_{MAX}$

The $\Delta AUC$ and $\Delta C_{MAX}$ are indicated in Table 2. There was no variation in the $\Delta AUC$ of each TCAA dosage group when compared with that of the control group. When the $\Delta C_{MAX}$ of 600 mg/kg TCAA group was compared to that of the control group, it was significantly inhibited (p<0.05). The $\Delta AUC$ and $\Delta C_{MAX}$ obtained from post-maltose-loading blood glucose values are indicated in Table 2.

TABLE 2

$\Delta AUC$ and $\Delta C_{MAX}$ Obtained From Post-Maltose-Loading Blood Glucose Levels

|  | $\Delta AUC$ (mg/dL · min) | $\Delta Cmax$ (mg/dL) |
|---|---|---|
| Control Group (Maltose Only) | 5603 ± 709 | 101 ± 7 |
| +TCAA 600 mg/kg × 2 | 5495 ± 300 | 73 ± 3* |
| +TCAA 300 mg/kg × 2 | 5456 ± 249 | 84 ± 5 |
| +TCAA 150 mg/kg × 2 | 5834 ± 484 | 86 ± 9 |

Mean ± Standard Error (n = 5)

*p < 0.05/significant change when compared to the control group (student's test)

7. Discussion

After the maltose employed in the present experiment was orally-ingested, it was degraded into a monosaccharide (glucose) via the action of α-glucosidase existing in the brush border membrane of the small intestine in the upper portion of gastrointestinal tract, to cause a rise in blood glucose. Here, when the influence of TCAA on blood glucose levels with respect to maltose-loading in a normal healthy rat was investigated, the significant inhibition of a drastic increase in blood glucose levels 15 minutes afterwards that was seen in the control group, was obvious in each TCAA dosage group. Moreover, the fact that TCAA inhibited the $C_{MAX}$ without any variation in the AUC indicated that the abovementioned component is capable of inhibiting a drastic increase in blood glucose levels after a meal, via the gradual absorption of glucose.

Example 5

Review of Water-Ethanol Mixture Ratio and TCAA Extraction Efficiency

Figure 5:
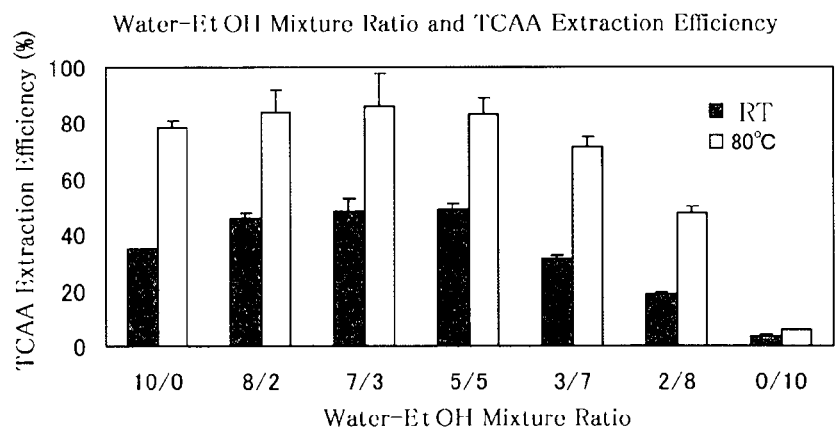
FIG. 5 is a graph showing a TCAA extraction efficiency and water-ethanol mixing ratio.

Yacon leaves and stems (10 g) were placed into 200 ml of each respective ratio of a water-ethanol mixed solution, it was then filtered through gauze after being agitated for 15 minutes, the filtrate therefrom was concentrated and lyophilized to prepare an extract, and the amount of TCAA was determined. A graph of the water-ethanol mixture ratio and TCAA extraction efficiency is indicated in FIG. 5. In the present experiment, when extracted with a mixed solution of ethanol and water, in which the concentration of ethanol is no less than 0% (v/v) to no greater than 70% (v/v), at both room temperature and 80° C., a superior TCAA extraction efficiency was achieved. Moreover, a superior TCAA extraction efficiency was achieved from an ethanol concentration of no less than 20% (v/v) to no greater than 70% (v/v). Furthermore, a more superior TCAA extraction efficiency was achieved from an ethanol concentration of no less than 30% (v/v) and/or no greater than 50% (v/v). Additionally, the most superior TCAA extraction efficiency was achieved from an ethanol concentration of 30% (v/v).

Example 6

Review of Extraction Temperature and TCAA Extraction Efficiency

Figure 6:
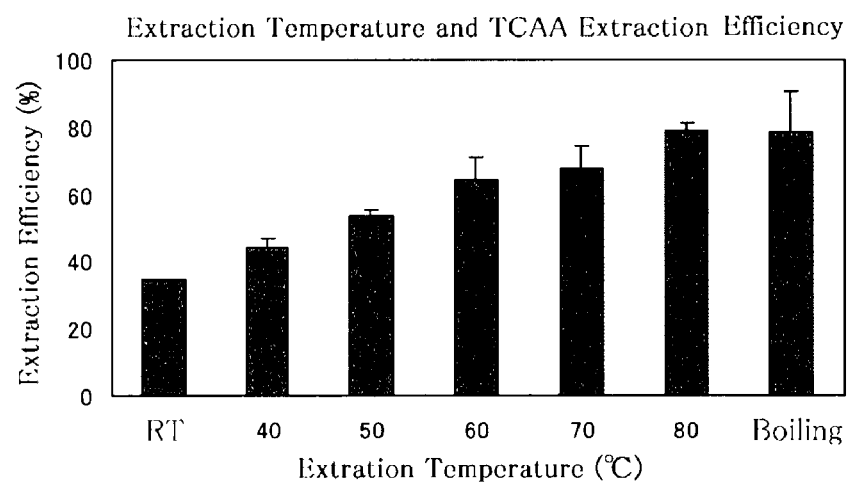
FIG. 6 is a graph showing a TCAA extraction efficiency and extraction temperature.

Yacon leaves and stems (10 g) were placed into 200 ml of water at each respective temperature, filtered through gauze after being agitated for 15 minutes, the filtrate therefrom concentrated and lyophilized to prepare an extract, and the amount of TCAA determined. A graph of the extraction temperature and TCAA extraction efficiency is indicated in FIG. 6. In the present experiment, uniform extraction efficiency was obtained within a temperature range of no less than room temperature (25° C.) to no greater than the boiling temperature (100° C.). From the standpoint of ease of handling, it is preferable that the temperature employed is not the boiling temperature (no greater than 90° C.). Moreover, a more preferable TCAA extraction efficiency was obtained with a temperature no less than 40° C., and an even more superior TCAA extraction efficiency was obtained with a temperature is no less than 60° C. to no greater than 80° C. Furthermore, the most superior TCAA extraction efficiency was obtained with a temperature of 80° C.

Example 7

Review of Extraction Solution pH and TCAA Extraction Efficiency

Figure 7:
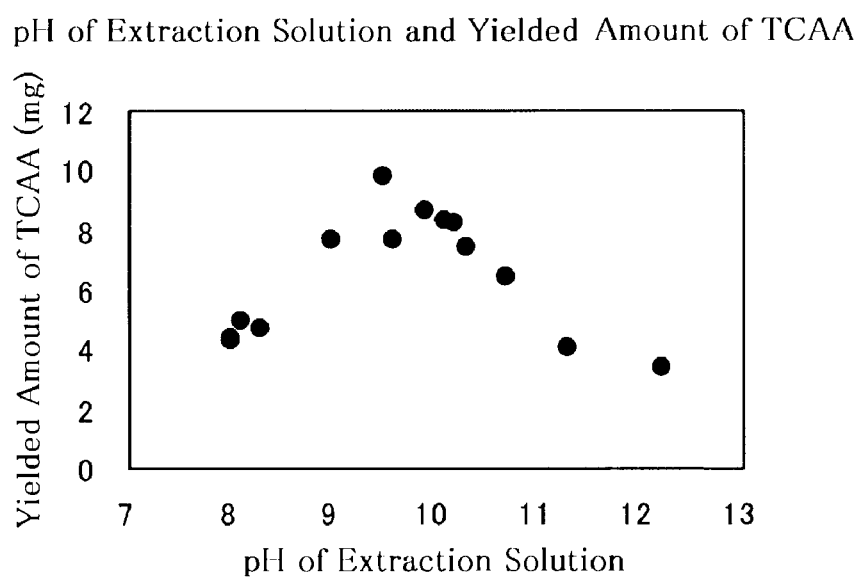
FIG. 7 is a graph showing a TCAA extraction efficiency and pH of an extraction liquid.

Solvent was added in amount of 200 ml per 10 g of Yacon leaves and stems, filtered through gauze after being agitated for 15 minutes, the filtrate therefrom concentrated and lyophilized to prepare an extract, and the amount of TCAA determined. The yielded amount of TCAA was calculated as the TCAA concentration within the extract multiplied by the yield amount to give the total amount of TCAA. A graph of the extraction solution pH and TCAA extraction efficiency is indicated in FIG. 7. In the present experiment, superior extraction efficiency was obtained when the pH of the extraction solution was no less than pH 8 to no greater than pH 11. Moreover, even more superior extraction efficiency was obtained when the pH of the extraction solution was no less than pH 8 to no greater than pH 10. Additionally, in the present example, aqueous ammonia (concentration of 0.028% to 0.28%), or aqueous sodium hydroxide (concentration of 0.01 N to 0.1 N), or aqueous sodium carbonate (concentration of 0.01 M to 0.1 M) may be employed as the solvent.

As mentioned above, the present invention was explained with reference to the Examples. Moreover, these Examples are solely illustrative, with various modifications thereof being possible, and it being understood by one who is skilled in the art that such modifications are thusly also to be included within the scope of the present invention.

REFERENCE DOCUMENTS

Reference Document 1: Ohnishi M., Morishita H., Toda S., Yase Y., Kido R., Phytochemistry, 47, 1215-1218 (1998);

Reference Document 2: Ohkawa H., Ohnishi N., Yagi K., Anal. Biochem., 95, 351-358 (1979);

Reference Document 3: Blois M. S., Nature, 181, 1199-1200 (1958);

Reference Document 4: Kweon M. H., Hwang H. J., Sung H. C., J. Agric. Food Chem., 49, 4646-4655 (2001);

Reference Document 5: Solon S., Lopes L., Teixera deSousa P. Jr., Schmeda-Hirschmann G., J. Ethnopharmacol., 72, 173-178 (2000);

Reference Document 6: Kahkonen M. P., Hopia A. I., Vuorela H. J., Rauha J. P., Pihlaja K., Kujala T. S., Heinonen M., J. Agric. Food Chem., 47, 3954-3962 (1999);

Reference Document 7: Takenaka M., Yan X., Ono H., Yoshida M., Nagata T., Nakanishi T., J. Agric. Food Chem., 51, 793-796 (2003);

Reference Document 8: Takenaka M., Ono H., Nagata T., Kameyama M., Yan X., Kokai Tokkyo Koho., JP 2001-19664 (2001);

Reference Document 9: Okuda T., Hatano T., Agata I., Nishibe S., Kimura K., YAKUGAKU ZASSHI, 106, 894-899 (1986);

Reference Document 10: Clifford M. N. and Kellard B., Food Chemistry, 34, 81-88 (1989); and Reference Document 11: Adeghate E., and Parvez S. H., Toxicicology, 153, 143-156 (2000); Uchiyama K., Naito Y., Hasegawa G., Nakamura N., Takahashi J., Yoshikawa T., Redox Rep., 7, 290-293 (2002);Lapidot T., Walker M. D., Kanner J., J. Agric. Food Chem., 50, 7220-7225 (2002).

The invention claimed is:

1. A food, comprising sodium tricaffeoylaldarate; and a health food ingredient or a nutritional ingredient.

2. The food of claim 1, wherein the sodium tricaffeoylaldarate is obtained from Yacon.

3. The food of claim 2, wherein the sodium tricaffeoylaldarate is obtained from leaves, stems or a combination of leaves and stems from Yacon.

4. The food of claim 2, wherein the sodium tricaffeoylaldarate is obtained from an extract extracted from Yacon with a solvent comprising a hydrophilic organic solvent or water.

5. The food of claim 1, further comprising dicaffeoylquinic acid.

6. The food of claim 1, further comprising a food additive.

* * * * *